United States Patent [19]

Rosenberg

[11] Patent Number: 5,126,132

[45] Date of Patent: Jun. 30, 1992

[54] TUMOR INFILTRATING LYMPHOCYTES AS A TREATMENT MODALITY FOR HUMAN CANCER

[75] Inventor: Steven A. Rosenberg, Bethesda, Md.

[73] Assignee: The United States of America as represented by the Department of Health and Human Services, Washington, D.C.

[21] Appl. No.: 396,528

[22] Filed: Aug. 21, 1989

[51] Int. Cl.$^5$ ...................... A61K 35/12; A61K 37/02
[52] U.S. Cl. ..................................... 424/93; 424/534; 424/85.2
[58] Field of Search ........................ 424/93, 534, 85.2; 530/351; 514/2.21

[56] References Cited

U.S. PATENT DOCUMENTS 4,690,915  9/1987  Rosenberg .......................... 424/534

OTHER PUBLICATIONS

Topalian et al, J. Immunol. Methods, 102, (1987), 127–141.
Belldegrun et al, Cancer Research, 46, (1986), 206–214.
Rosenberg et al, Science, vol. 233, (1986), 1318–1321.

*Primary Examiner*—Jacqueline Stone
*Attorney, Agent, or Firm*—Mishrilal Jain

[57] ABSTRACT

A new immunotherapeutic method of treating cancer with a combination of tumor infiltrating lymphocytes and IL-2 has been described.

6 Claims, 5 Drawing Sheets

TUMOR INFILTRATING LYMPHOCYTES AS A TREATMENT MODALITY FOR HUMAN CANCER

The present invention is related generally to the field of cancer treatment. More particularly, the present invention is related to providing immunotherapy to cancer patients using a combination of tumor infiltrating lymphocytes and interleukin-2.

Conventional chemotherapy is relatively ineffective in the treatment of patients with metastatic cancer. There were about 800,000 cases of invasive cancer in the USA in 1988 and about 6,000 patients die of this disease in the USA each year. An effective therapy of patients with malignancy is much needed.

SUMMARY OF THE INVENTION

It is, therefore, an object of the present invention to provide an effective immunotherapy for treating cancer in humans.

It is a further object of the present invention to provide a combination of tumor infiltrating lymphocytes (TIL) and interleukin-2 (IL-2) for the treatment of malignancy in humans.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the detailed description of the invention when considered in connection with the accompanying drawings which show as follows:

FIG. 4: Photographs of a 21-year old male who had a large recurrent growth of melanoma in his left neck following a radical neck dissection.

FIG. 6: Photographs of the chest well of a 38-year old woman who had multiple cutaneous metastases following resection of melanoma.

DETAILED DESCRIPTION OF THE INVENTION

Figure 1:
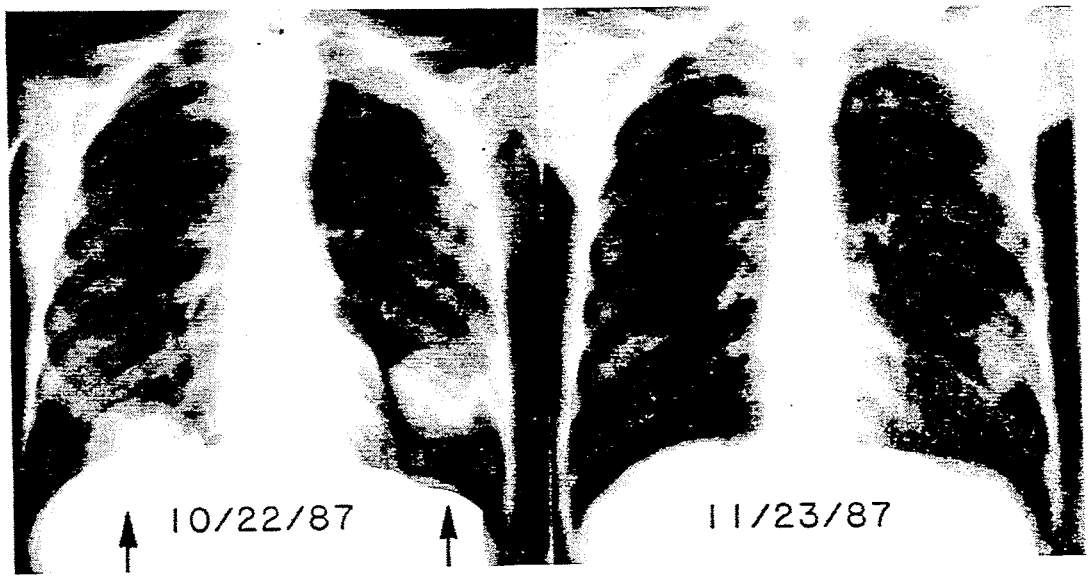
FIG. 1: Lung metastases in a 38-year old female before treatment (left) and following one course of tumor infiltrating lymphocyte therapy (right). The chest film on the right shows substantial regression of the metastases. Multiple subcutaneous metastases regressed in this patient as well.
Figure 2:
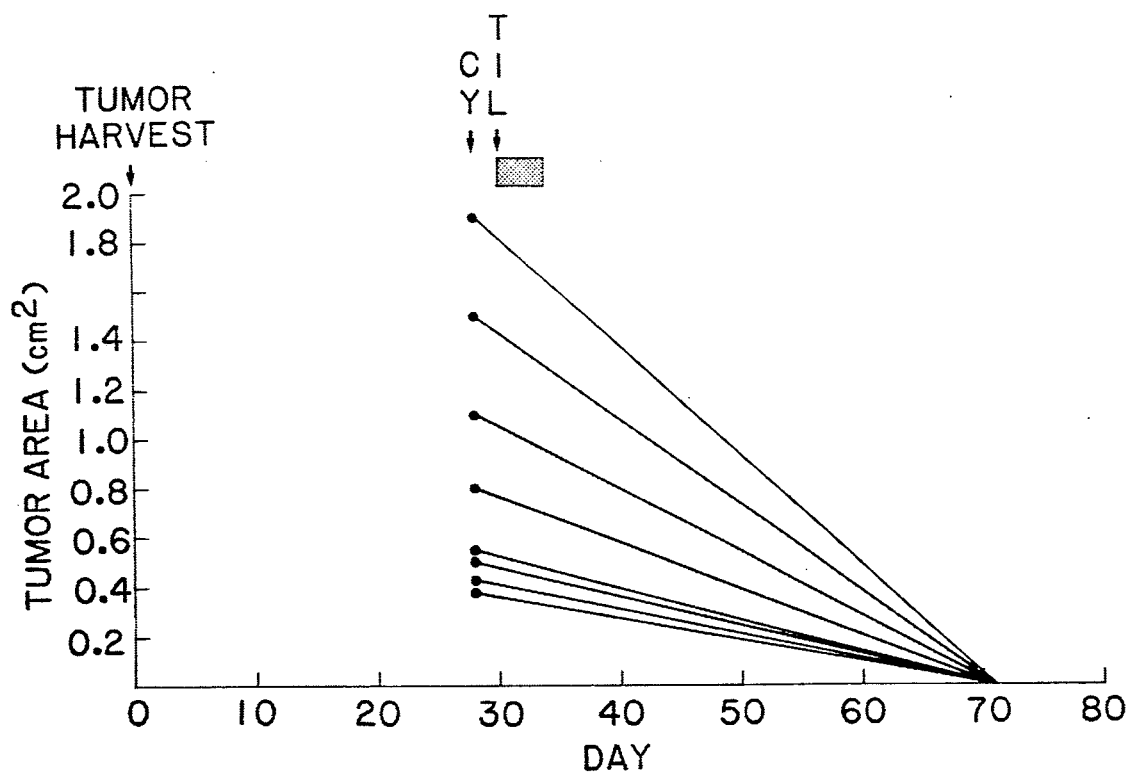
FIG. 2: Diagram showing complete disappearance of multiple subcutaneous metastases in a 56-year old male following TIL therapy. This patient had multiple subcutaneous metastases, all of which regressed following treatment.
Figure 3:
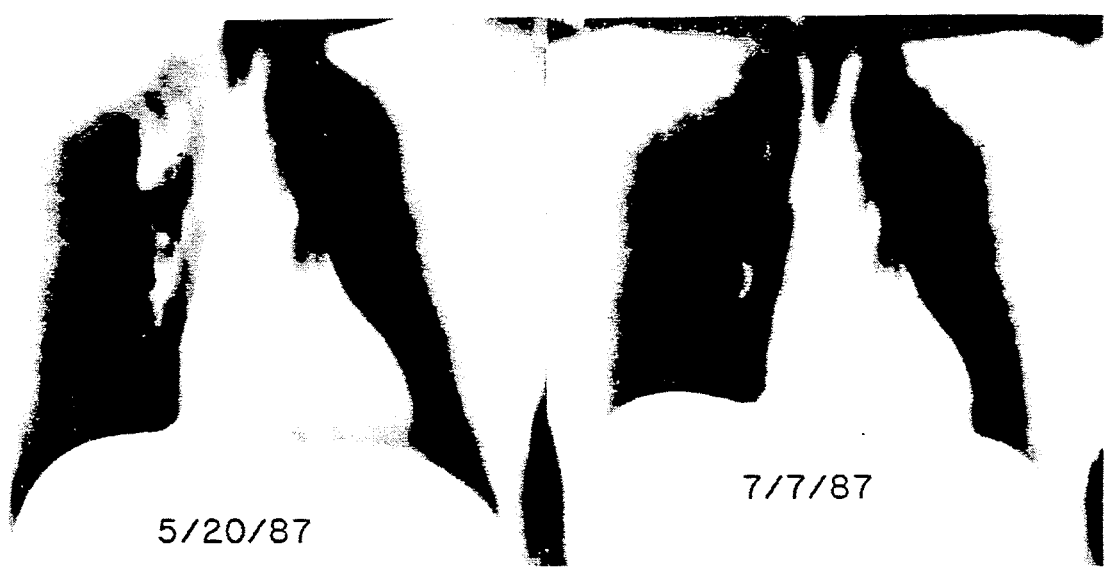
FIG. 3: Regression of a lung metastasis in a 46-year old woman following therapy with TIL. The x-ray on the left shows a mass in the right upper lung that underwent substantial regression following TIL therapy as shown in the x-ray on the right.
Figure 4A:
FIG. 4a shows the neck mass prior to treatment and FIG. 4b shows complete regression of this mass in the neck following TIL therapy.
Figure 4B:
Figure 5A:
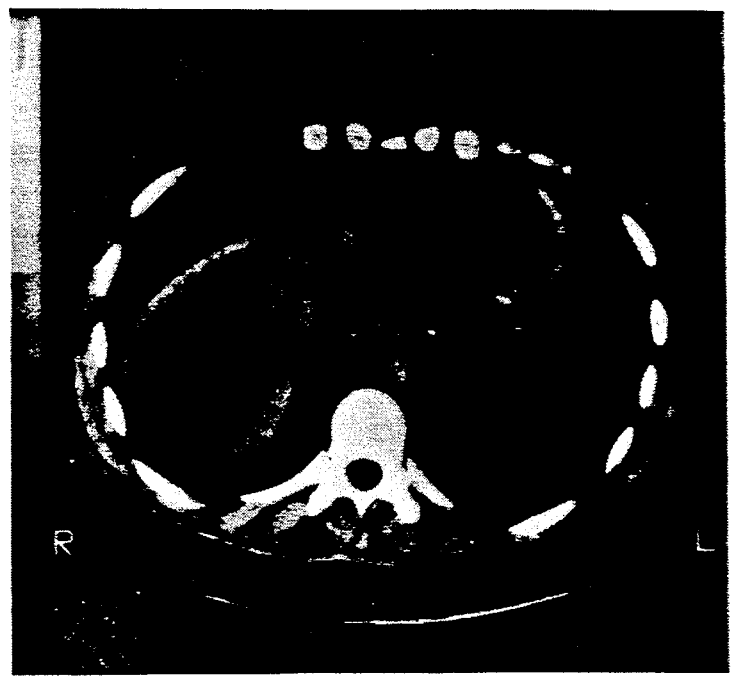
FIG. 5a shows a CAT scan of the liver showing a large lesion replacing the right lobe of the liver. This lesion underwent substantial regression following a single course of TIL therapy (FIG. 5b).
Figure 5B:
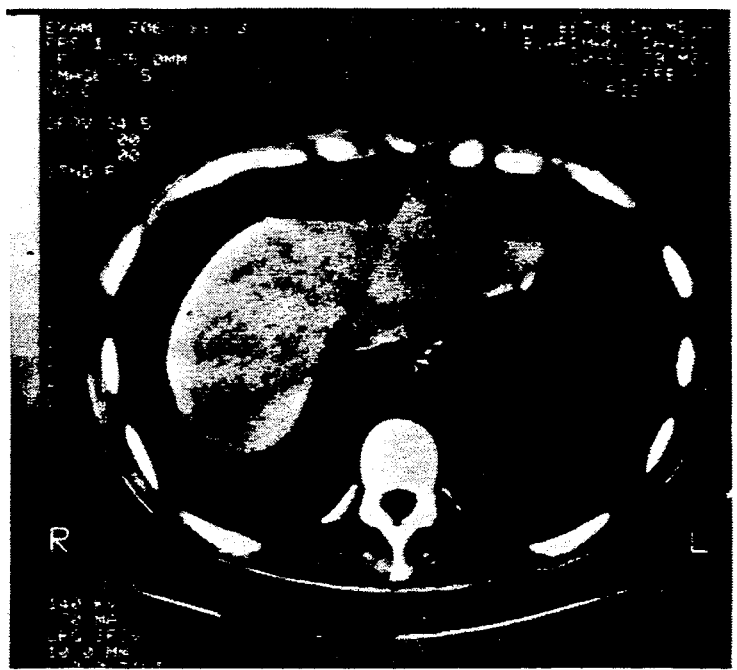
FIG. 5: The same patient shown in FIG. 4. This patient also had several large liver metastases.
Figure 6A:
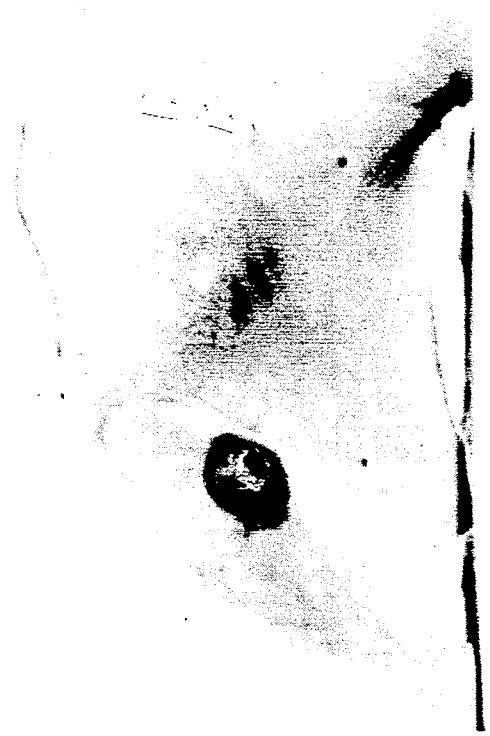
FIG. 6a shows a large cutaneous metastases on the right chest wall as well as a large growing metastatic deposit on a skin graft that had been used to cover the resected right breast.
Figure 6B:
FIG. 6b shows substantial regression of these subcutaneous metastases following TIL therapy.

The above and various other objects and advantages of the present invention are achieved by a method of treating malignancy in humans, comprising administering an effective amount of TIL and IL-2 to a patient afflicted with cancer to cause regression of the cancer.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The general approach is the development of a treatment for patients with cancer using the transfer of immune lymphocytes that are capable of reacting with and destroying the cancer. In this invention tumors that are removed from patients with cancer are used for the isolation of lymphocytes that were infiltrating into that tumor. These lymphocytes are grown in culture to large numbers and then reinfused back into the patient along with the administration of interleukin-2. The treatment is intended to reduce or eliminate cancer in the patient.

Tumors are resected from patients with cancer and single cell suspensions are produced using enzymatic digestion. These single cell suspensions consist largely of tumor cells but with occasional infiltrating lymphocytes. These single cell suspensions are then cultured in tissue culture medium (either RPMI-1640 or AIM-5 serum free medium) in the presence of interleukin-2. Lymphocytes that bear interleukin-2 receptors react with interleukin-2 and begin to grow. As these lymphocytes grow they destroy tumor cells and by approximately two weeks a pure culture of lymphocytes exists with no contaminating tumor cells. These lymphocytes are then cultured in the laboratory to large numbers. By four to six weeks after initiating the culture approximately $3 \times 10^{11}$ lymphocytes are obtained.

Patients with cancer are then treated with these tumor infiltrating lymphocytes along with the administration of interleukin-2. Experimental animal work has demonstrated that these tumor infiltrating lymphocytes can distribute directly to tumor and under the influence of administered IL-2 can remain alive in vivo. At the site of tumor these TIL destroy tumor either by direct contact or by the secretion of cytokines. In 20 patients reported in the New England Journal of Medicine 319:1676–1680, 1988, objective reference regression of advanced cancer (melanoma) was seen in 11 patients. Of 15 patients that had previously not been treated with immunotherapy, nine responded (60%). Of five patients that had previously failed therapy with IL-2 alone, two had cancer regressions (40%).

The details of patient selection, protocol and the results obtained are now described.

METHODS

Patients

All the patients had a diagnosis of metastatic malignant melanoma, which could be evaluated by physical or radiographic examination. Of the 20 patients in this study, 18 had undergone surgical excision, 5 had received chemotherapy that had failed, 3 had received radiotherapy, 5 had received therapy with interleukin-2, and 1 had received therapy with alfa-interferon. None had undergone any other form of therapy for their disease for 30 days before treatment according to the protocol, and none received treatment during the follow-up period. Patients with central nervous system metastases were excluded.

The procedures used for preparation of the tumor-infiltrating lymphocytes are detailed below At least two days prior to surgery, peripheral blood lymphocytes are collected by leukapheresis for four hours. These are Ficoll-Hypaque separated and the mononuclear cells collected from the interface, washed in saline, and placed in culture in roller bottles at $10^6$ cells/ml. Half are placed into AIMV (a serum free medium, Gibco Laboratories) with 1000 U/ml IL-2 (Cetus), and half are placed into RPMI supplemented with 2% type-compatible human serum, penicillin (unless the patient is allergic), gentamicin, and 1000 U/ml IL-2. After 3 to 4 days cells are centrifuged and the supernatants collected and filtered. These are referred to as LAK supernatants.

Immediately upon tumor resection, the specimen(s) is transported to the laboratory in a sterile container and placed on a sterile dissection board in a laminar blow hood. A small representative portion is taken for pathology, and the rest is minced into pieces roughly 4 mm maximum dimension. These are placed into an enzyme solution of collagenase, DNAse type I, and hyaluronidase type V (Topalian et al, *J. Immunol. Meth.* 102: 127-141, 1987) for overnight (about 12-16 hrs) digestion at room temperature (about 22°-24° C.). The resulting suspension is filtered through a wire mesh to remove any large debris, washed in saline, and placed on Ficoll-Hypaque gradients. The interface containing viable lymphocytes and tumor cells is collected and washed in saline, and a portion is frozen for subsequent use as targets.

TIL cultures are initiated at $5 \times 10^5$ ml viable cells (tumor plus lymphocytes) in 80% fresh medium/20% LAK supernatant. For half the cells, the fresh medium is AIMV supplemented with penicillin, fungizone, and 1000 U/ml IL-2; for the other half, the fresh medium is RPMI supplemented with 10% human serum, penicillin, gentamicin, fungizone, and 1000 U/ml IL-2. The cultures are placed into 6-well tissue culture dishes and incubated at 37° in humidified incubators with 5% $CO_2$.

Usually the lymphocyte density is not much increased at the end of seven days in culture, and the cultures are collected, centrifuged, and resuspended at $5 \times 10^5$ total viable cells/ml in newly prepared 80%/20%, median mixtures of the same type. Occasionally a culture will have increased lymphocyte density and need medium replenishment prior to seven days. After this first passage, TILs are subcultured by dilution when the density is between $1.5 \times 10^6$ and $2.5 \times 10^6$ ml; densities of subcultures are established between $3 \times 10^5$ and $6 \times 10^5$ ml. Cultures are kept in 6-well dishes when the volume is less than 1 liter, and transferred to 3 liter polyolefin bags (Fenwal) when the volume reaches 1 liter. The subcultures from bags are accomplished with Fluid Fill/Weight Units (Fenwal), which are programmed to pump certain weights of TIL culture and fresh medium into a new bag. When subculture volumes exceed 3 liters, the fresh medium used is AIMV. Cultures growing in serum-containing medium are thus diluted into AIMV, and no further LAK supernatant is added to cultures growing in serum-containing or serum-free medium.

When the total TILs for a patient are ready for infusion, $5 \times 10^6$ cells are taken for cytological examination. Cytospins are stained with antibodies to leukocyte common antigen and to tumor antigens, and examined for the presence of remaining tumor. At least 200 cells are studied and therapy proceeds only when no tumor cells are found. Other TIL samples are taken for characterization of cell surface markers and for assessment of cytotoxicity. Briefly, TILs are stained with fluorescent-labeled antibodies (Leu2, Leu3, Leu4, Leu7, Leu11, Leu15, Leu19, LeuM3, HLADR, and Tac). Chromium release assays are performed with K562, Daudi, autologous tumor, and allogeneic tumor targets.

The total TILs are collected in two or more batches by continuous flow centrifugation (CS-3000 blood cell separators, Fenwal). Following cell collection, 1 liter of saline for injection is pumped through the collection chamber and the centrifuge is stopped. TILs are resuspended in the collection bag, the centrifuge is started again, and another liter of saline is pumped through to fully wash the TILs free of tissue culture medium components. TILs are filtered through a platelet administration set into 600 ml transfer packs (Fenwal), and 50 ml of 25% albumin and 25,000 units of IL-2 are added to the 200 to 300 ml volume of cells in saline. A 0.5 ml aliquot is taken to Clinical Pathology for a stat gram stain and routine culture, and cells are released for therapy only if not organisms are seen on the gram stain.

Protocol

Tumor deposits were resected, usually under local anesthesia; most resected tumors weighed between 10 and 30 g. TIL were expanded in culture for four to eight weeks, according to techniques described herein supra. When the TIL were ready for infusion, patients first received a single intravenous dose of cyclophosphamide (25 mg per kilogram of body weight) and 36 hours later the first intravenous infusion of TIL in an intensive care unit; a maximum of $2 \times 10^{11}$ cells were administered in 200 to 250 ml over a period of 30 to 60 minutes. Each patient received a total of one to seven infusions over one to two days, depending on the number of cells to be administered and the time required to harvest the cells. After the first infusion of TIL, the patients began receiving recombinant interleukin-2 (Cetus Corporation, Emeryville, Calif.) (100,000 units per kilogram, given intravenously every eight hours in 50 ml of 0.9 percent saline with 5 percent albumin). (Rosenberg et al. *Science*, 1984; 223:1412-4.) Interleukin-2 was administered until dose-limiting toxicity occurred; some doses were omitted depending on the patient's tolerance. The side effects of interleukin-2 administration were treated with acetaminophen, indomethacin, ranitidine, and meperidine as described by Rosenberg et al (*N. Eng J Med*, 1987; 316:889-97).

Assessment of Response to Treatment

A response was considered to be complete if all measurable tumor disappeared, and to be partial if the sum of the products of the longest perpendicular diameters of all lesions decreased by at least 50 percent and if no tumor had any increase and no new tumor appeared. The term "objective responses" refers to the sum of complete and partial responses.

RESULTS

Studies in murine tumor models had indicated that successful therapy with TIL depended on prior administration of cyclophosphamide, although this is not necessarily required in humans (Rosenberg et al, *Science*, 1986; 223:1318–21). Thus, to determine the degree of tolerance and response to cyclophosphamide plus interleukin-2 without administration of TIL, these clinical studies were begun by treating a series of 13 patients with metastatic melanoma with various doses of cyclophosphamide (4 patients with 50 mg per kilogram, 6 with 25 mg per kilogram, and 3 with 10 mg per kilogram) followed 36 hours later by infusion of interleukin-2 (100,000 units per kilogram every eight hours). On the basis of this preliminary evaluation, a dose of 25 mg per kilogram was selected for the TIL therapy because it was the highest dose that resulted in acceptable levels of hematologic suppression when given with interleukin-2. Partial responses were observed in 2 of the 13 patients (1 patient who received 50 mg per kilogram and 1 who received 10 mg per kilogram)--results similar to those expected using treatment with interleukin-2 alone.

The characteristics of the 20 patients with metastatic melanoma treated with cyclophosphamide, TIL, and interleukin-2 and the characteristics of their treatment and response are shown in Table 1. The number of TIL infused ranged from $3 \times 10^{10}$ to $75 \times 10^{10}$ cells (median, $20.5 \times 10^{10}$; 25th percentile, $12.9 \times 10^{10}$; 75th percentile, $29.8 \times 10^{10}$). Of the 15 patients who had never before been treated with interleukin-2, 9 (60 percent) had objective evidence of cancer regression. Of the five patients in whom interleukin-2-based therapies had previously failed, two (40 percent) had objective responses. Regression of cancer was observed at a variety of sites, including the lungs (FIG. 1), liver, spleen, lymph node, bone, and subcutanneous tissue. Two of these responding patients (Patients 8 and 9) received a second course of therapy with cyclophosphamide, TIL, and interleukin-2, and four (Patients 3 through 6) received a second course of interleukin-2 alone approximately two months after the first course of cyclophosphamide, TIL, and interleukin-2. All these patients, however, had objective responses after the first course of treatment. The duration of the responses ranged from 2 to more than 13 months.

The toxicity of the treatment is summarized in Table 2. Chills were the only toxic effect associated with TIL infusion and were easily controlled with meperidine. Most toxi effects were attributable to the interleukin-2 infusions and appeared to be related to an increased vascular permeability that led to loss of intravascular volume and accumulation of fluid in visceral organs and soft tissues (Rosenstein et al, *J. Immunol*, 1986; 137:1735–42). No patient died of treatment. The side effects all resolved after interleukin-2 was discontinued, and the median time from the end of treatment to hospital discharge was four days (25th percentile, three day; 75th percentile, seven days). Toxicity was lower in this regimen than in others using this dose of interleukin-2, because the treatment time was shorter (median, 5 days; 25th percentile, 4 days; 75th percentile, 6 days) than the 15 days required for a course of therapy with LAK cells plus interleukin-2.

Tumor cells were obtained from 17 patients (other than the 20 patients listed in Table 1), but no treatment was given to them--7 patients because of debilitation caused by the progression of their disease, 8 because of poor lymphocyte growth, and 2 because of contamination of cultures by bacteria. Three other patients not listed in Table 1 had brain metastases that developed between the time of tumor harvest and the time of final TIL growth; they received TIL, but because of their poor performance status at the time of treatment their doses of interleukin-2 were reduced. One of these patients died 13 days after infusion of TIL, with metastases involving the brain and virtually all visceral organs. Another patient had a decrease in cutaneous metastases and a decrease in brain metastases on CT scans obtained one month after treatment. This patient died at home one month later of what appeared to be an intracerebral event, although no autopsy was performed.

Studies of the adoptive transfer of TIL in murine tumor models have shown that these cells are 50 to 100 times more effective than LAK cells in mediating tumor regression (Rosenberg et al, *Science*, 1986, 223:1318–21; Spiess et al, *JNCI*, 1987; 79:1067–75). In contrast to LAK cells, TIL obtained from mice and patients are predominantly T lymphocytes, and those from patients are often capable of lysing autologous melanoma in a fashion that is highly specific and restricted by the major histocompatibility complex (Muul et al, *J Immunol*, 1987, 138:989–95; Itoh et al, *Cancer Res*, 1986, 46:3011–7; Kurnick et al, *Clin Immunol Immunopathol*, 1986, 38:367–80; Rabinowich et al, *Cancer Res*, 1987, 47:173–7; Miescher et al, *J Immunol*, 1987, 138:4004–11; Topalian et al, *J Immunol Methods*, 1987, 102:127–41; Belldegrun et al, *Cancer Res*, 1988, 48:206–14). As with other forms of experimental adoptive therapy with T cells, immunosuppression of the tumor-bearing host with either cyclophosphamide or total-body irradiation is required for treatment to be successful (Berendt et al, *J Exp Med*, 1980, 151:69–80; Shu et al, *J Immunol*, 1985, 135:2895–903; Eberlein et al, *J Exp Med*, 1982, 156:385–97). This pretreatment is thought to eliminate suppressor cells or to facilitate lymphocyte "homing." Cyclophosphamide administration or total-body irradiation does not affect treatment with LAK cells in murine models.

Therefore, 13 patients were first treated with the combined administration of cyclophosphamide and interleukin-2, and observed only two objective responses (15 percent), in accord with the response expected with the use of interleukin-2 alone. However, the addition of TIL to the combination of cyclophosphamide and interleukin-2 resulted in responses in 9 of 15 patients (60 percent) who had not previously been treated with interleukin-2 and in 2 of 5 patients (40 percent) in whom treatment with interleukin-2 had previously failed (both patients had previously received a different preparation of recombinant interleukin-2). It thus appears that treatment with TIL increased response rates among patients with metastatic melanoma, as compared with therapy with LAK cells and interleukin-2, cyclophosphamide and interleukin-2, or interleukin-2 alone. The results reported here reflect primarily the results of a single cycle of treatment with TIL.

Since only 1 of the 11 responding patients had a complete response, perhaps more intensive or repeated therapy might improve the quality of response.

The shorter course of treatment with TIL and interleukin-2 (5 days as compared with 15 days for therapy with LAK cells and interleukin-2) was better tolerated by the patients. There were no treatment-related deaths among the 20 patients described here, although 1 to 3 patients with brain metastases treated with lower doses of interleukin-2 died 13 days after therapy, with extensive intracranial, visceral, and cutaneous disease. All side effects occurring in these 20 patients resolved after the completion of therapy.

Extensive immunologic studies have been performed on the initial suspensions of tumor cells and on the infused TIL to determine the requirements for successful therapy. The great majority of the infused TIL were CD3+, though the relative number of CD4+ and CD8+ cells varied among the patients (Table 1). Cultures of TIL exhibited varying patterns of cytotoxicity, proliferation, and lymphokine production, though no pattern has yet emerged to predict the TIL populations that will mediate cancer regression in vivo. Moreover, a study of TIL traffic in six patients with melanoma who each received a small aliquot of indium-111-labeled TIL revealed subs antial homing of TIL to cancer deposits [Fisher et al, *J Clin Oncol* (in press)].

In summary, the present study does demonstrate that the adoptive transfer of immune autologous cells can be effective in mediating cancer regression and further emphasizes the need to pursue the development of this biologic approach to cancer therapy.

It is understood that the examples and embodiments described herein are for illustrative purposes only and that various modifications or changes in light thereof will be suggested to persons skilled in the art and are to be included within the spirit and purview of this application and scope of the appended claims. These changes include the combined administration of TIL with other cytokines such as interferon or with other cancer treatments such as chemotherapy or radiotherapy.

What is claimed is:

1. A method of treating cancer in humans, comprising administering to humans afflicted with cancer that respond to immunotherapy, an, effective amount of autologous tumor infiltrating lymphocytes (TIL) and a cytokine to prevent metastasis or cause regression of cancer.

2. The method of claim 1 wherein said cytokine is IL-2.

3. The method of claim 2 wherein the effective amount of TIL ranges from about $5 \times 10^9$ to $5 \times 10^{11}$ cells and IL-2 ranges from about 10,000 to 100,000 units per kilogram body weight.

4. The method of claim 2 wherein an effective amount of cyclophosphamide is administered to patient prior to TIL-IL2 infusion.

5. The method of claim 4 wherein the amount of cyclophosphamide ranges from about 10 to 50 mg per kilogram body weight.

6. The method of claim 1 wherein said cancer is melanoma, lung, liver, cutaneous or subcutaneous metastases.

* * * * *